United States Patent

Girard et al.

[11] Patent Number: 5,036,067
[45] Date of Patent: Jul. 30, 1991

[54] DIBENZOHETEROCYCLIC HYDROXAMIC ACIDS AND HYDROXY UREAS AS INHIBITORS OF 5-LIPOXYGENASE

[75] Inventors: Yves Girard; Pierre Hamel; Daniel Delorme, all of Quebec, Canada

[73] Assignee: Merck & Co., Inc., Rahway, N.J.

[21] Appl. No.: 493,527

[22] Filed: Mar. 14, 1990

[51] Int. Cl.$^5$ .............. A61K 31/54; A61K 31/55; C07D 279/18; C07D 281/12

[52] U.S. Cl. .............. 514/224.8; 514/211; 514/431; 514/434; 514/436; 540/551; 544/350; 544/38; 544/39; 549/10; 549/11; 549/12; 549/16; 549/17

[58] Field of Search .............. 540/551; 544/35, 38, 544/39; 549/10, 11, 12, 16, 17; 514/211, 224.8, 431, 434, 436

[56] References Cited

U.S. PATENT DOCUMENTS

| | | | |
|---|---|---|---|
| 3,519,622 | 7/1970 | Sutton | 544/35 |
| 3,639,612 | 2/1972 | De Long | 544/35 |
| 4,536,507 | 8/1985 | Rokach et al. | 514/364 |
| 4,576,940 | 3/1986 | Tahara et al. | 514/212 |
| 4,666,907 | 5/1987 | Fortin et al. | 514/223 |
| 4,822,811 | 4/1989 | Summers | 514/411 |
| 4,839,354 | 6/1989 | Sunshine et al. | 514/226.5 |
| 4,845,083 | 7/1989 | Fortin et al. | 514/80 |
| 4,873,259 | 10/1989 | Summers et al. | 514/443 |
| 4,889,874 | 12/1989 | Haslanger et al. | 514/575 |

FOREIGN PATENT DOCUMENTS

0279263 2/1988 European Pat. Off. .
87/04152 12/1986 United Kingdom .
2191194A 6/1987 United Kingdom .

OTHER PUBLICATIONS

P. K. Kadaba, The Synthesis of Some Phenothiazinyl Ketones and Their Derivatives, *J. Het. Chem.* 3, 345 (1966).

C. M. Suter, et al., The Directive Influences of Oxygen and Sulfur, *J.A.C.S.* 58, 717 (1936).

*Primary Examiner*—C. Warren Ivy
*Assistant Examiner*—Celia Chang
*Attorney, Agent, or Firm*—Hesna J. Pfeiffer; Gabriel Lopez

[57] ABSTRACT

Compounds having the formula I:

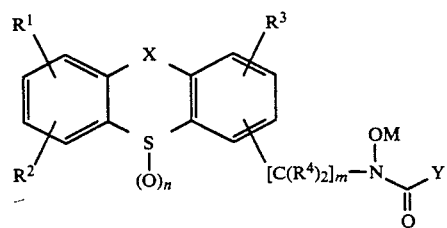

are inhibitors of the 5-lipoxygenase enzyme. These compounds are useful as anti-asthmatic, anti-allergic, anti-inflammatory, and cytoprotective agents. They are also useful in treating diarrhea, hypertension, angina, platelet aggregation, cerebral spasm, premature labor, spontaneous abortion, dysmenorrhea, and migraine.

9 Claims, No Drawings

DIBENZOHETEROCYCLIC HYDROXAMIC ACIDS AND HYDROXY UREAS AS INHIBITORS OF 5-LIPOXYGENASE

BACKGROUND OF THE INVENTION

The leukotrienes and their biological activities, especially their role in various disease states, have been extensively studied. Their properties are described in the book *Leukotrienes and Lipoxygenase*, Ed., J. Rokach, Elsevier, N.Y., 1989.

Inhibitors of the 5-lipoxygenase enzyme will prevent the biosynthesis of the various leukotrienes, and hence have a beneficial effect in those disease states in which the leukotrienes contribute to the disease.

Various derivatives of hydroxylamine have been described as inhibitors of the 5-lipoxygenase enzyme. Representative compounds are to be found in the following patent documents: EP 196,184, EP 279,263, WP 87/04152, U.K. 2,191,194 and U.S. Pat. No. 4,822,811.

SUMMARY OF THE INVENTION

The present invention relates to compounds having activity as inhibitors of the 5-lipoxygenase enzyme, to methods for their preparation, and to methods and pharmaceutical formulations for using these compounds in mammals (especially humans).

Because of their activity as inhibitors of 5-lipoxygenase, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to inhibit the pathologic actions of leukotrienes on the cardiovascular and vascular systems for example, actions such as result in angina or endotoxin shock. The compounds of the present invention are useful in the treatment of inflammatory and allergic diseases of the eye, including allergic conjunctivitis. The compounds are also useful as cytoprotective agents and for the treatment of migraine headache.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma-or stress-induced cell damage; and glycerol-induced renal failure.

The compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus inhibition of the synthesis of such compounds will alleviate these and other leukotriene-related disease states.

DETAILED DESCRIPTION OF THE INVENTION

The compounds of the present invention are represented by formula I:

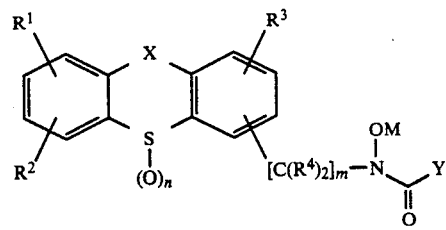

Wherein:

$R^1$, $R^2$ and $R^3$ are independently:
  a) hydrogen,
  b) lower alkyl,
  c) lower cycloalkyl,
  d) lower alkoxy,
  e) lower alkanoyloxy;
  f) —$CF_3$
  g) —CN,
  h) —$NO_2$,
  i) —$OR^4$,
  j) —$N(R^4)_2$, —$NCOR^4$, —$N(R^4)CON(R^4)_2$,
  k) —$SR^5$, —$S(O)R^5$, —$S(O)_2R^5$, —$S(O)_2NR^4$,
  l) —$COR^4$, —$COOR^4$, —$CON(R^4)_2$,
  m) halogen;

$R^4$ is:
  a) hydrogen,
  b) $R^5$;

$R^5$ is:
  a) $C_1$-$C_4$ alkyl;

$R^6$ is:
  a) hydrogen,
  b) $C_1$ to $C_4$ alkyl,
  c) —$COR^4$,
  d) —$S(O)_2R^4$,
  e) —$C_1$-$C_4$; alkylene-Ar $R^7$ is:
  a) hydrogen,
  b) lower alkyl,
  c) Ar-lower alkyl, Ar is:
  a) $R^1$ substituted phenyl,
  b) $R^1$ substituted furyl,
  c) $R^1$ substituted thienyl;

X is:
  a) $X^1$,
  b) —CH=CH—,
  c) —$CH_2$—$CH_2$—,
  d) —$CH_2X^1$—,
  e) —$X^1CH_2$—,
  f) $NR^7$;

$X^1$ is:
  a) O,
  b) S,
  c) S(O),
  d) $S(O)_2$,
  e) $NR^6$;

Y is:
  a) $R^4$,
  b) —$N(R^4)_2$;

M is:
  a) hydrogen,
  b) —COAr,
  c) —CO—alkyl;

m is 1 to 5;
n is 0 to 2;
and pharmaceutically acceptable salts thereof.

Alkyl, alkenyl, and alkynyl are intended to include linear and branched structures and combinations thereof.

As used herein, the term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

As used herein, the term "lower alkyl" includes those alkyl groups of from 1 to 7 carbon atoms. Examples of lower alkyl groups include methyl, ethyl, propyl, isopropyl, butyl, sec- and tert-butyl, pentyl, hexyl, heptyl, and the like.

The term "cycloalkyl" refers to a hydrocarbon containing one or more rings having from 3 to 12 carbon atoms, with the hydrocarbon having up to a total of 20 carbon atoms. Examples of cycloalkyl groups are cyclopropyl, cyclopentyl, cycloheptyl, aldamantyl, cyclododecylmethyl, 2-ethyl-1-bicyclo[4.4.0]decyl and the like.

"Cycloalkenyl" groups include those alkenyl groups of 3 to 20 carbon atoms, which include a ring of 3 to 12 carbon atoms, and in which the alkenyl double bond may be located anywhere in the alkenyl group. Examples of cycloalkenyl groups are cyclopropen-1-yl, cyclohexen-3-yl, 2-vinyladamant-1-yl, 5-methylenedodec-1-yl, and the like.

As used herein, the term "lower alkoxy" includes those alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

As used herein the term "lower alkylthio" includes those alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies $-SCH_2CH_2CH_3$; "lower alkylsulfinyl" and "lower alkylsulfonyl" refer to the sulfoxides and sulfones of "lower alkylthio".

Halogen includes F, Cl, Br, and I.

It is intended that the definitions of any substituent (e.g., $R^1$, $R^2$, $R^3$, etc.) in a particular molecule be independent of its definitions elsewhere in the molecule. Thus, $-N(R^3)_2$ represents $-NH_2$, $-NHCH_3$, $-N(CH_3)C_2H_5$, etc.

The term "alkanoyl" refers to the acyl residue of an alkanoic acid of up to 20 carbon atoms. Examples, of alkanoyl groups include formyl, acetyl, 2-ethylhexanoyl, eicosanoyl, etc. The term "aroyl" refers to the acyl residue of a benzoic acid carrying an $R^1$ substituent. Examples of aroyl groups include benzoyl, 4-chlorobenzoyl, 3-cyanobenzoyl, etc.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, $N,N^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

The ability of the compounds of Formula I to inhibit the 5-lipoxygenase enzyme makes them useful for inhibiting the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary conditions including diseases such as asthma, 2) allergies and allergic reactions such as allergic rhinitis, contact dermatitis, allergic conjunctivitis, and the like, 3) inflammation such as arthritis or inflammatory bowel disease, 4) pain, 5) skin conditions such as psoriasis and the like, 6) cardiovascular conditions such as angina, endotoxin shock, and the like and 7) renal insufficiency arising from ischaemia induced by immunological or chemical (cyclosporin) etiology and that the compounds are cytoprotective agents.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |
| Tablet | mg/tablet |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |
| Aersol canister | Per |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives;
(5) the oxicams or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

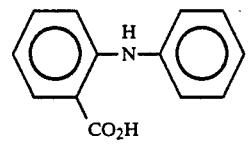

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

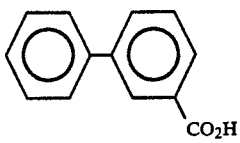

which can bear a variety of substituents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

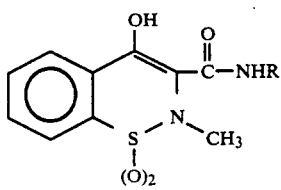

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used:
480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (July 21, 1982) and 61,800 (June 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as a-fluoromethylhistidine, described in U.S. Pat. No. 4,325,961. The compounds of the Formula I may also be advantageously combined with an $H_1$ or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the formula I of the present invention may be prepared according to the following method. Temperatures are in degrees Celsius, and compound numbers relate to those represented in Scheme 1 below.

The hydroximinoalkyl intermediate III is prepared by addition of hydroxylamine hydrochloride to the ketone II in an alcoholic solvent, such as ethanol, in the presence of an organic nitrogen base, e.g. pyridine. The oxime, III, is then converted to the hydroxaminoalkyl IV by reduction with a suitable reducing agent, such as pyridine-borane complex, in an acidic alcoholic solvent, e.g. ethanolic HCl. Compounds of the formula I are then obtained from IV by addition of trimethylsilyl isocyanate in an organic solvent such as tetrahydrofuran (THF). Subsequent addition of water allows the necessary hydrolysis to the N-hydroxy urea compounds I of the invention. This portion of the synthesis is repeated below, from the ketone intermediate II, with several variations on the starting material.

For example, phenoxathiin ketone II may be taken through to I directly or first oxidized by an oxidant, such as m-chloroperoxy benzoic acid (MCPBA), in an organic solvent, such as methylene chloride, followed by addition of an inorganic base, such as calcium hydroxide, to yield the phenoxathiin-10,10-dioxide ketone V. This compound may then be treated like II above to yield the N-[1-(10,10-dioxo-phenoxathiin-2-yl)ethyl]-N-hydroxy urea compound of formula I.

Where $R^1$ is hydrogen and $R^2$ is bromine (or chlorine), addition of a compound of formula VI halophenoxathiin, to a suspension of aluminum chloride in 1,2-dichloro ethane in the presence of an acyl halide, (followed by quenching with ice-water and isolation of the organic fraction and drying over $MgSO_4$) yields the halogenated ketone II which may then be treated as was II above to yield the N-[1-(8-halophenoxathiin-2-yl)ethyl]-N-hydroxy urea of formula I.

In order to incorporate a cyano functionality into the 8 position of the molecule, the haloketone, as obtained above, may be treated with cuprous cyanide in an organic solvent, such as DMF, followed by precipitation in water and isolation of the organic components. The resultant 8-cyano ketone II may then be treated as was the ketone II above to yield I as, for example, the N-[1-(8-cyanophenoxathiin-2-yl)ethyl]-N-hydroxy urea derivative.

Where the starting material contains a carboxylic acid moiety VII, as in dibenzo[b,f]thiepin-3-carboxylic acid and similar compounds, the acid group may be converted into the ketone of formula II by treatment with methyl lithium in ether followed by aqueous ammonium chloride and isolation of the organic phase. The ketone thus derived may then be treated as was II above to yield, for example, the N-[1-(Dibenzo[b,f]thiepin-3-yl)ethyl]-N-hydroxy urea of formula I.

Where $R^1$ is hydrogen and $R^2$ is carboxy, a compound of formula V, such as the 2-acetyl-5, 5-dioxo-10,11-dihydro dibenzo [b,f]thiepin-7-carboxylic acid, in an organic solvent such as ethyl acetate, may be esterified by addition of a solution of diazomethane in ether to yield the methyl ester ketone V. This compound may then be treated like II above to yield the N-[1-(7-carbomethoxy-5,5-dioxo-10,11-dihydro dibenzo[b,f]thiepin-2-yl)ethyl]-N-hydroxy urea of formula I.

Where $R^1$ is hydrogen and $R^2$ is carbomethoxy, a compound of formula I, such as N-[1-(7-carbomethoxy-5,5-dioxo-10,11-dihydro dibenzo [b,f] thiepin-2-yl) ethyl]-N-hydroxy urea, may be hydrolyzed by base, such as aqueous sodium hydroxide, in an alcoholic solvent, such as ethanol to yield the N-[1-(7-carboxy-5,5-dioxo-10,11-dihydro dibenzo [b,f] thiepin-2-yl)ethyl]-N-hydroxy urea.

Alternatively, the carbomethoxy derivative of formula I, may be converted to the carboxamide by treatment with N,N-dimethylamino dimethyl aluminum in toluene. Quenching by addition of excess ethyl acetate followed by acidification yields the N-[1-(7-dimethylcarboxamide-5,5-dioxo-10,11-dihydro dibenzo [b,f]thiepin-2-yl)ethyl]-N-hydroxy urea.

The method described above may be applied to the starting ketone II wherein X is a nitrogen, as in 2-acetylphenothiazine which may be treated directly as the ketone II above or derivatized first to yield compounds of formula VIII. The derivatization may be accomplished by addition of potassium t-butoxide to the ketone II in DMF. Subsequent addition of methyl iodide, 4-methylthiobenzyl chloride, 4-methylsulfonylbenzyl chloride, or other such alkylating groups followed by addition of ice-water and isolation of the organic phase, allows the preparation of the ketone with the substituted nitrogen. This ketone may then be treated as was II above to generate the hydroxy urea of formula I.

Incorporation of a halogen into the substituted nitrogen compounds VIII just described is most conveniently achieved by using the halogenated starting material, for example, the 2-chloro-8-acetylphenothiazine ketone or the 2-chloro-8,10-diacetylphenothiazine ketone, and then proceeding as for the ketone II above.

SCHEME I

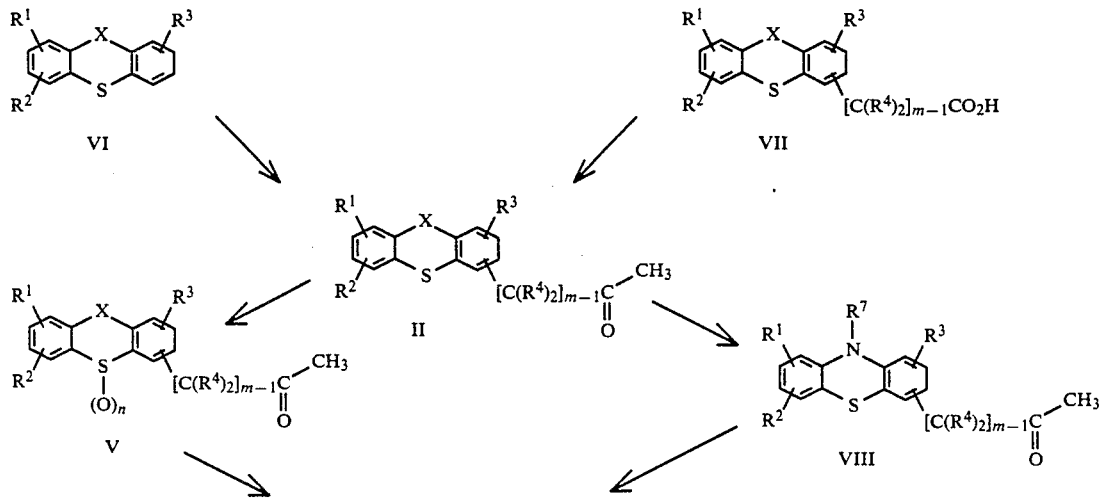

-continued
SCHEME I

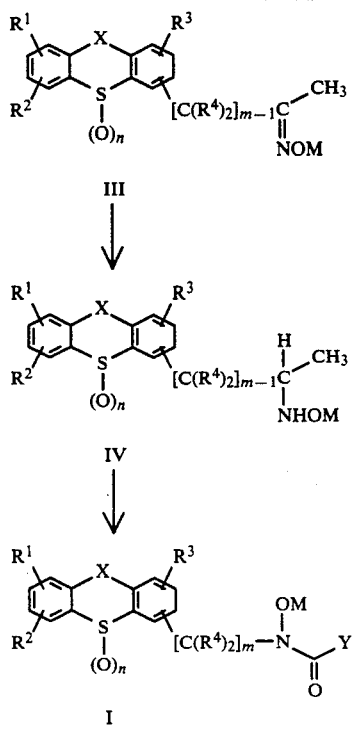

Representative Compounds

Compounds of formula IX and X are representative of the invention wherein the substituents are as defined in Tables I and II respectively:

TABLE I

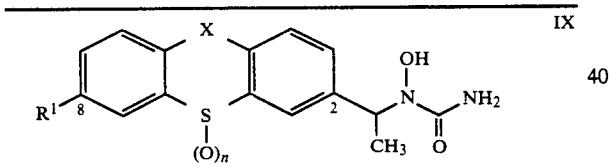

IX

| EXAMPLE # | X | n | R¹ |
|---|---|---|---|
| 1 | O | 0 | H |
| 2 | O | 2 | H |
| 3 | O | 0 | Cl |
| 4 | O | 0 | Br |
| 5 | O | 0 | CN |
| 9 | CH₂O | 0 | H |

TABLE II

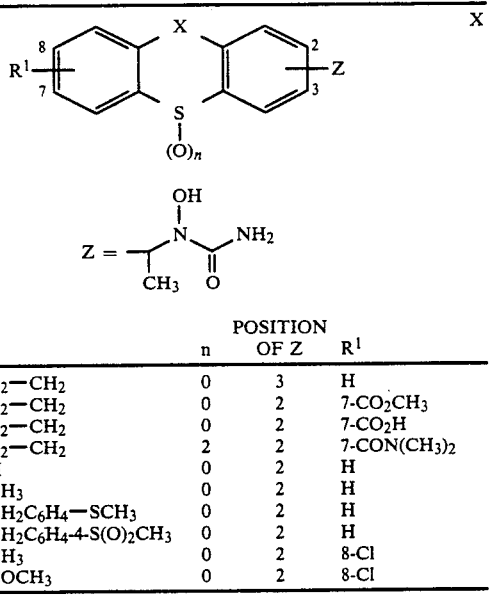

X

| EX # | X | n | POSITION OF Z | R¹ |
|---|---|---|---|---|
| 6 | CH=CH | 0 | 3 | H |
| 7 | CH=CH | 2 | 3 | H |

TABLE II-continued

X

| EX # | X | n | POSITION OF Z | R¹ |
|---|---|---|---|---|
| 8 | CH₂—CH₂ | 0 | 3 | H |
| 10 | CH₂—CH₂ | 0 | 2 | 7-CO₂CH₃ |
| 11 | CH₂—CH₂ | 0 | 2 | 7-CO₂H |
| 12 | CH₂—CH₂ | 2 | 2 | 7-CON(CH₃)₂ |
| 13 | NH | 0 | 2 | H |
| 14 | NCH₃ | 0 | 2 | H |
| 15 | NCH₂C₆H₄—SCH₃ | 0 | 2 | H |
| 16 | NCH₂C₆H₄-4-S(O)₂CH₃ | 0 | 2 | H |
| 17 | NCH₃ | 0 | 2 | 8-Cl |
| 18 | NCOCH₃ | 0 | 2 | 8-Cl |

Assays for Determining Biological Activity

Compounds of Formula I can be tested using the following assays to determine their mammalian leukotriene biosynthesis inhibitory activity.

Determination of Inhibition of 5-Lipoxygenase

The activity of 5-lipoxygenase was measured from the conversion of [$^{14}$C]-arachidonic acid to 5-HETE and 5,12-diHETEs catalyzed by the 10,000×g supernatant fraction from rat PMN leukocytes, using the procedure of Riendeau and Leblanc (*Biochem. Biophys. Res. Commun.*, 141, 534–540, 1986) with minor modifications. The incubation mixture contained 25 mM Na+/K+ phosphate buffer, pH 7.3, mM ATP, 0.5 mM CaCl$_2$, 0.5 mM mercaptoethanol and an aliquot of the enzyme preparation in a final volume of 0.2 ml. The enzyme was pre-incubated with the inhibitor for 2 min at 37° C. before initiation of the reaction with the addition of 2 ml of [$^{14}$C]-arachidonic acid (25,000 DPM) in ethanol to obtain a final concentration of 10 mM. Inhibitors were added as 500-fold concentrated solutions in DMSO. After incubation for 10 min at 37° C., the reaction was stopped by adding 0.8 mL of diethyl ether/methanol/1 M citric acid (30:4:1). The samples were centrifuged at 1,000×g for 5 min and the organic phases analyzed by TLC on Baker Si250F-PA or Whatman silica gel 60A LKGF plates using diethyl ether/petroleum ether/acetic acid (50:50:1) as solvent. The amount of radioactivity migrating at the positions of arachidonic acid, 5-HETE and 5,12-diHETEs was determined using a Berthold TLC analyzer LB 2842. The activity of 5-lipoxygenase was calculated from the percentage of conversion of arachidonic acid to 5-HETE and 5,12-diHETEs after the 10 min incubation.

Rat Peritoneal Polymorphonuclear (PMN) Leukocyte Assay

Rats under ether anesthesia are injected (i.p.) with 8 mL of a suspension of sodium caseinate (6 grams in ca. 50 mL water). After 15-24 hr. the rats are sacrificed (CO$_2$) and the cells from the peritoneal cavity are recovered by lavage with 20 mL of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/mL. A 500 mL aliquot of PMN suspension and test compound are preincubated for 2 minutes at 37°, followed by the addition of 10 mM A-23187. The suspension is stirred for an additional 4 minutes then bioassayed for LTB$_4$ content by adding an aliquot to a second 500 mL portion of the PMN at 37° C. The LTB$_4$ produced in the first incubation causes aggregation of the second PMN, which is measured as a change in light transmission. The size of the assay aliquot is chosen to give a submaximal transmission change (usually −70%) for the untreated control. The percentage inhibition of LTB$_4$ formation is calculated from the ratio of transmission change in the sample to the transmission change in the compound-free control.

Human Polymorphonuclear (PMN) Leukocyte LTB$_4$ Assay

A. Preparation of Human PMN: Human blood was obtained by antecubital venepuncture from consenting volunteers who had not taken medication within the previous 7 days. The blood was immediately added to 10% (v/v) trisodium citrate (0.13M) or 5% (v/v) sodium heparin (1000 IU/mL). PMNs were isolated from anticoagulated blood by dextran sedimentation of erythrocytes followed by centrifugation through Ficoll-Hypaque (specific gravity 1.077), as described by Boyum.[1] Contaminating erythrocytes were removed by lysis following exposure to ammonium chloride (0.16M) in Tris buffer (pH 7.65), and the PMNs resuspended at 5×10$^5$ cells/mL in HEPES (15 mM)-buffered Hanks balanced salt solution containing Ca$^{2+}$ (1.4 mM) and Mg$^{2+}$ (0.7 mM), pH 7.4. Viability was assessed by Trypan blue exclusion and was typically greater than 98%.

(1) Boyum, A. Scand. J. Clin. Lab. Invest. 1968, 21 (Supp 97), 77.

B. Generation and Radioimmunoassay of LTB$_4$: PMNs (0.5 mL; 2.5×10$^5$ cells) were placed in plastic tubes and incubated (37° C., 2 min) with test compounds at the desired concentration or vehicle (DMSO, final concentration 0.2%) as control. The synthesis of LTB$_4$ was initiated by the addition of calcium ionophore A23187 (final concentration 10 mM) or vehicle in control samples and allowed to proceed for 5 minutes at 37° C. The reactions were then terminated by the addition of cold methanol (0.25 mL) and samples of the entire PMN reaction mixture were removed for radioimmunoassay of LTB$_4$.

Samples (50 mL) of authentic LTB$_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter [$^3$H]-LTB$_4$ (10 nCi in 100 mL RIA buffer) and LTB$_4$-antiserum (100 mL of a 1:3000 dilution in RIA buffer) were added and the tubes vortexed. Reactants were allowed to equilibrate by incubation overnight at 4° C. To separate antibody-bound from free LTB$_4$, aliquots (50 mL) of activated charcoal (3% activated charcoal in RIA buffer containing 0.25% Dextran T-70) were added, the tubes vortexed, and allowed to stand at room temperature for 10 minutes prior to centrifugation (1500×g; 10 min; 4° C.). The supernatants containing antibody-bound LTB$_4$ were decanted into vials and Aquasol 2 (4 mL) was added. Radioactivity was quantified by liquid scintillation spectrometry. Preliminary studies established that the amount of methanol carried into the radioimmunoassay did not influence the results. The specificity of the antiserum and the sensitivity of the procedure have been described by Rokach et al.[2] The amount of LTB$_4$ produced in test and control (approx. 20 ng/10$^6$ cells) samples were calculated. Inhibitory dose-response curves were constructed using a four-parameter algorithm and from these the IC$_{50}$ values were determined.

(2) Rokach, J.; Hayes, E. C.; Girard, Y.; Lombardo, D. L.; Maycock, A. L.; Rosenthal, A. S.; Young, R. N.; Zamboni, R.; Zweerink, H. J. *Prostaglandins Leukotrienes and Medicine* 1984, 13, 21.

Asthmatic Rat Assay

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mgm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

EXAMPLES

The invention is further defined by reference to the following examples, which are intended to be illustrative and not limiting. All temperatures are in degress Celsius.

EXAMPLE 1

N-[1-(Phenoxathiin-2-yl)ethyl]-N-hydroxy urea

Step 1: 2-(1-Hydroximinoethyl)phenoxathiin

A mixture of 2-acetylphenoxathiin (J.A.C.S. 1936, 58, 717) (484 mg, 2 mmol), hydroxylamine hydrochloride (556 mg, 8 mmol), ethanol (8 mL) and pyridine (4 mL) was stirred at room temperature for 45 minutes. The ethanol was evaporated and the residue triturated with water until a solid was obtained. Filtration afforded the title oxime (465 mg) as a cream-colored solid, m.p.: 143°–148° C.

Step 2: 2-(1-Hydroxaminoethyl)phenoxathiin

The oxime from Step 1 (450 mg, 1.75 mmol) was suspended in ethanol (9 mL) and, at 0° C., there was added pyridine-borane (325 mg, 3.5 mmol) and 4M ethanolic hydrogen chloride (HCl) (1.33 mL, 5.32 mmol). The mixture was stirred at 0° C. for 20 minutes, then at room temperature for 1 hour. The ethanol was evaporated and the residue partitioned between water and ether. The aqueous portion was basified with 1N aqueous sodium hydroxide and extracted twice with ether. Drying of the ether and evaporation afforded the title product (408 mg) as an oil which slowly became a white solid, m.p.: 64°–67° C.

Step 3: N-[1-(Phenoxathiin-2-yl)ethyl]-N-hydroxy urea

To a solution of the product from Step 2 (250 mg, 0.965 mmol) in tetrahydrofuran (THF, 4 mL) there was added 85% trimethylsilyl isocyanate (196 mg, 1.45 mmol) and the solution was stirred at room temperature for 1 hour. Water (4 mL) was added, stirring was continued for 10 minutes, then the THF was evaporated; the residue was extracted twice with ether and the crude product obtained from evaporation of the extracts was crystallized from ether to afford the title compound as white crystals, m.p.: dec 155° C. with gassing.

Analysis: Calc'd for $C_{15}H_{14}N_2O_3S$: C, 59.58; H, 4.67; N, 9.27; S, 10.61. Found: C, 59.72; H, 4.66; N, 9.50; S, 10.34.

EXAMPLE 2

N-[1-(10,10-Dioxophenoxathiin-2-yl)ethyl]-N-hydroxy urea

Step 1: 2-Acetylphenoxathiin-10,10-dioxide

To a solution of 2-acetyl phenoxathiin (J.A.C.S. 1936, 58, 717) (484 mg, 2 mmol) in methylene chloride (25 mL) there was added 85% m-chloroperoxy benzoic acid (MCPBA 1.015 g, 5 mmol) and the mixture stirred at room temperature. After 3 hours, more MCPBA was added (250 mg) and stirring was continued for a further hour. Enough methylene chloride was added to dissolve the solids, followed by calcium hydroxide (3 g); after stirring for a further 5 minutes, the mixture was filtered and the filtrate evaporated to a solid residue which was triturated with ether (10 mL) and filtered to afford the sulfone (415 mg) as a white solid, m.p.: 163°–165° C.

Step 2: N-[1-(10,10-Dioxophenoxathiin-2-yl)ethyl]-N-hydroxy urea

Following the procedure of Example 1, Steps 1–3, but substituting the ketone from Step 1 for 2-acetylphenoxathiin as starting material, the title compound was obtained as an off-white solid, m.p.: dec 188° C. with strong gassing.

EXAMPLE 3

N-[1-(8-Chlorophenoxathiin-2-yl)ethyl]-N-hydroxy urea

Step 1: 2-Chloro-8-(1-hydroxaminoethyl)phenoxathiin

To a suspension of 2-chloro-8-(1-hydroximinoethyl)-phenoxathiin (C.A. 66, 2519a, 1967) (425 mg, 1.456 mmol) in ethanol (12 mL) and THF (5 mL) at room temperature there was added pyridine-borane (271 mg, 0.3 mL, 2.92 mmol) and 4M ethanolic HCl (1.1 mL, 4.4 mmole); the mixture was stirred at room temperature overnight, there was added more pyridine-borane (0.35 mL) and 4M ethanolic HCl (2 mL) and stirring was continued for 2 hours. The solvents were evaporated, the residue diluted with water and ethyl acetate and basified with 1N aqueous NaOH. From the organic phase a crude product was obtained which was chromatographed on silica gel, eluting with a 1:1 mixture of ethyl acetate-hexane, to afford the title product (344 mg) as a white solid, m.p.: 103°–105° C.

Step 2
N-[1-(8-Chlorophenoxathiin-2-yl)ethyl]-N-hydroxy urea

To a solution of the product from Step 1 (320 mg, 1.09 mmol) in THF (15 mL) there was added 85% trimethylsilyl isocyanate (295 mg, 2.18 mmol) and the mixture was stirred at room temperature for 45 minutes. After addition of water (5 mL) the mixture was stirred a further 10 minutes, then the THF was evaporated, the residual aqueous suspension diluted with water and filtered to afford the title compound as a white solid, m.p.: dec 173° C. (gassing).

EXAMPLE 4

N-[1-(8-Bromophenoxathiin-2-yl)ethyl]-N-hydroxy urea

Step 1: 2-Acetyl-8-bromophenoxathiin

To a suspension of aluminum chloride (1.2 g, 9 mmol) in 1,2-dichloro ethane (20 mL) at room temperature there was added acetyl chloride (0.57 mL, 628 mg, 8 mmol) and the mixture stirred for 10 minutes. There was added 2-bromophenoxathiin (J.A.C.S. 1936, 58, 717) (1.8 g, 6.4 mmol) and the mixture was stirred for 18 hours. After quenching with ice water, the organic portion was collected and the aqueous portion extracted with methylene chloride. The combined organic fractions, after washing 3 times with water and drying over $MgSO_4$, were evaporated to a residue which on crystallization from methanol, followed by column chromatography on silica gel, eluting with a 1:5 mixture of ethyl acetate-hexane, gave the title product as a white solid (247 mg), m.p.: 143°–145° C.

Step 2: N-[1-(8-Bromophenoxathiin-2-yl)ethyl]-N-hydroxy urea

Following the procedures described in Example 1, Steps 1–3 but, substituting the ketone from Step 1 for 2-acetylphenoxathiin as the starting material, the title product was obtained as a white solid, m.p.: dec 171° C.

EXAMPLE 5

N-[1-(8-Cyanophenoxathiin-2-yl)ethyl]-N-hydroxy urea

Step 1: 2-Acetyl-8-cyanophenoxathiin

A mixture of 2-acetyl-8-bromophenoxathiin (from Example 4, Step 1) (1.73 g, 5.39 mmol) and cuprous cyanide (1.94 g, 21.6 mmol) in N,N-dimethylformamide (DMF, 15 mL) was refluxed for 7 hours. After cooling, the mixture was diluted with water and the precipitated solid filtered. This solid was boiled with ethyl acetate (100 mL) and filtered. The process was repeated with THF (100 mL, then 50 mL) and the combined filtrates evaporated to afford a yellow solid. This was purified by column chromatography on silica gel, eluting with a 1:3 mixture of ethyl acetate-hexane, to afford the title nitrile (774 mg) as a yellow solid, m.p.: 179°–183° C.

Step 2: N-[1-(8-Cyanophenoxathiin-2-yl)ethyl]-N-hydroxy urea

Following the procedures described in Example 1, Steps 1–3, but substituting the ketone from Step 1 for 2-acetylphenoxathiin as the starting material, the title product was obtained as a cream-colored solid, m.p.: 162° dec with gassing.

EXAMPLE 6

N-[1-(Dibenzo[b,f]thiepin-3-yl)ethyl]-N-hydroxy urea

Step 1: 3-Acetyldibenzo[b,f]thiepin

To a solution of dibenzo[b,f]thiepin-3-carboxylic acid (U.S. Pat. No. 4,536,507 (1985)) (415 mg, 1.63 mmole) in THF (20 mL) at 0° C. there was added methyl lithium in ether 1.4M (2.56 mL, 3.59 mmol); the mixture was stirred at 0° C. for 1 hour, then poured onto a well-stirred saturated aqueous ammonium chloride solution (100 mL). The organic phase was collected, washed twice with brine, dried and evaporated. Column chromatography on silica gel, eluting with a 1:2 mixture of ethyl acetate-hexane, afforded the title compound as a yellow solid (320 mg), m.p.: 82°–84° C.

Step 2: N-[1-Dibenzo[b,f]thiepin-3-yl)ethyl]-N-hydroxy urea

Following the procedure described in Example 1, Steps 1–3, but substituting the ketone from Step 1 for 2-acetylphenoxathiin as starting material, the title compound was obtained as a white solid, m.p.: dec 169° C. with gassing.

EXAMPLE 7

N-[1-(5,5-Dioxodibenzo[b,f]thiepin-3-yl)ethyl]-N-hydroxy urea

Following the procedures described in Example 2, Steps 1–2, but substituting 3-acetyldibenzo[b,f]thiepin (Example 6, Step 1) for 2-acetyl phenoxathiin as starting material, the title compound was obtained as a sand-colored solid, m.p.: dec 188° with strong gassing.

EXAMPLE 8

N-[1-(10,11-Dihydrodibenzo[b,f]thiepin-3-yl)ethyl]-N-hydroxy urea

Following the procedure described in Example 6, Steps 1–2 but substituting 10,11-dihydrodibenzo[b,f]thiepin-3-carboxylic acid (U.S. Pat. No. 4,536,507 (1985)) for dibenzo[b,f]thiepin-3 -carboxylic acid as starting material, the title product was obtained as a cream-colored solid, m.p.: 166°–168° C.

EXAMPLE 9

N-[1(6H-Dibenz[b,e][1,4]oxathiepin-2-yl]ethyl]-N-hydroxy urea

Following the procedure described in Example 6, Steps 1–2 but substituting 6H-dibenz[b,e]-[1,4]oxathiepin-2-carboxylic acid (EP Pat. 105692 (1984)) for dibenzo[b,f]thiepin-3-carboxylic acid as starting material, the title compound was obtained as a cream-colored solid, m.p.: dec 141° C..

EXAMPLE 10

N-[1-(7-Carbomethoxy-10,11-dihydrodibenzo[b,f]-thiepin-2-yl)ethyl]-N-hydroxy urea Step 1:Methyl 2-acetyl-10,11-dihydrodibenzo-[b,f]thiepin-7-carboxylate To a solution of 2-acetyl-10,11-dihydro-dibenzo[b,f]-thiepin-7-carboxylic acid (U.S. Pat. No. 4,536,507 (1985)) (600 mg, 2.01 mmol) in ethyl acetate (10 mL), was added dropwise a solution of diazomethane in ether until the yellow coloration persisted. Evaporation of the solvent gave the crude title compound as a solid which was used as such.

Step 2:N-[1-(7-Carbomethoxy-10,11-dihydrodibenzo[b,f]-thiepin-2-yl)ethyl]-N-hydroxy urea Following the procedure described in Example 1, Steps 1–3 but substituting the ketone from Step 1 for 2-acetylphenoxathiin as starting material, the title product was obtained, m.p.: 167°–169° C..

EXAMPLE 11

N-[1-(7-Carboxy-10,11-dihydrobibenzo[b,f]thiepin-2-yl)ethyl]-N-hydroxy urea

To a solution of N-[1-(7-carbomethoxy-10,11-dihydrodibenzo[b,f]thiepin-2-yl)-ethyl]-N-hydroxy urea from Example 10 (50 mg, 0.134 mmol) in ethanol (1 mL) was added at room temperature a solution of NaOH 1N (0.4 mL, 0.402 mmol) and the resulting mixture was then stirred for 16 hours. A solution of 1N HCl was then added until the reaction mixture became slightly acidic. The resulting mixture was diluted with THF (50 mL) dried over $MgSO_4$ and evaporated. The residue was triturated with ethyl acetate and the solid was filtered to afford the title compound, m.p.: 178°–180° C.

EXAMPLE 12

N-[1-(7-Dimethylcarboxamido-5,5-dioxo-10,11-dihydrodibenzo[b,f]thiepin-2-yl)ethyl]-N-hydroxy urea Step 1 Methyl 2-acetyl-5,5-dioxo-10,11-dihydrodibenzo[b,f]thiepin-7-carboxylate Following the procedure described in Example 10, Step 1, but substituting 2-acetyl-5,5-dioxo-10,11-dihydrodibenzo[b,f]thiepin-7-carboxylic acid (U.S. Pat. No. 4,536,507 (1985)) for 2-acetyl-10,11-dihydrodibenzo[b,f]thiepin-7-carboxylic acid as starting material, the title product was obtained as a solid.

Step 2: N,N-Dimethyl 2-acetyl-5,5-dioxo-10,11-dihydrodibenzo[b,f]thiepin-7-carboxamide To a solution of the ester from Step 1 (440 mg, 1.28 mmol) in dry toluene (5 mL) was added dropwise at room temperature a solution of N,N-dimethylamino dimethyl aluminum 0.8M in toluene (16 mL, 12.8 mmol). The resulting solution was heated to 70° C. for 2 hours. The reaction mixture was then cooled to 0° C. and quenched with excess ethyl acetate followed by addition of 1N aqueous HCl. The solvents were removed under reduced pressure and the resulting solid was filtered, washed with ethyl acetate to afford the title product which was used as such for the next step.

Step 3: N-[1-(7-Dimethylcarboxamido-5,5-dioxo-10,11-dihydrodibenzo[b,f]thiepin-2-yl)ethyl]-N-hydroxy urea Following the procedure described in Example 1, Steps 1–3, but substituting the ketone from Step 2 for 2-acetylphenoxathiin as starting material, the title product was obtained as a cream-colored solid, m.p.: 174°–176° C. with previous sintering at 168° C.

EXAMPLE 13

N-[1-(Phenothiazin-2-yl)ethyl]-N-hydroxy urea

Following the procedure described in Example 1, Step 1–3, but substituting 2-acetylphenothiazine (Aldrich) for 2-acetylphenoxathiin as starting material, the title product was obtained as a cream-colored solid, m.p.: 150°–152° C. (dec).

EXAMPLE 14

N-[1-(10-Methylphenothiazin-2-yl)ethyl]-N-hydroxy urea

Step 1: 2-Acetyl-10-methylphenothiazine

To a solution of 2-acetylphenothiazine (Aldrich) (2.41 g, 10 mmol) in dimethylformamide (25 mL) was added potassium t-butoxide (1.5 g, 13.4 mmol) and the mixture was stirred for 15 minutes. Methyl iodide (1.9 g, 13.4 mmol) was then added, dropwise, to the resulting solution and the mixture stirred for 30 minutes. Ice-water was added to the reaction mixture followed by ethyl acetate. The organic layer was decanted, washed with brine, dried over $Na_2SO_4$ and evaporated to dryness. The oily residue was chromatographed on flash silica gel eluting with 10% ethyl acetate/hexane to afford the pure title product (1.0 g, 39%).

Step 2: N-[1-(10-Methylphenothiazin-2-yl)ethyl]-N-hydroxy urea

Following the procedure described in Example 1, Steps 1–3, but substituting the ketone from Step 1 for 2-acetylphenoxathiin as starting material, the title product was obtained, m.p.: 165°–167° C. (dec).

EXAMPLE 15

N-{1-[10-(4-Methylthiobenzyl)phenothiazin-2-yl]ethyl}-N-hydroxy urea

Following the procedure described in Example 14, Steps 1–2, but substituting 4-methylthiobenzyl chloride for methyl iodide as starting material, the title product was obtained as a foamy solid.

$^1$H NMR (250 MHz, acetone-$d_6$); Δ 1.32 (d, 3H, J=7 Hz, CHCH$_3$), 2.44 (S, 3H, SCH$_3$), 5.13 (S, 2H, CH$_2$), 5.25 (quartet, 1H, J=7 Hz, CH), 5.9 (broad S, 2H, NH$_2$), 6.9–7.4 (m, 11H, aromatics) and 8.3 (S, 1H, OH).

EXAMPLE 16

N-{1-[10-(4-Methylsulfonylbenzyl)phenothiazin-2-yl]ethyl}-N-hydroxy urea

Following the procedures described in Example 14, Steps 1–2, but substituting 4-methylsulfonylbenzyl chloride for methyl iodide as starting material, the title product was obtained, m.p.: 143°–145° C. with previous sintering at 132° C.

EXAMPLE 17

N-[1-(8-Chloro-10-methylphenothiazin-2-yl)ethyl]-N-hydroxy urea

Following the procedures described in Example 14, Steps 1–2, but substituting 2-acetyl-8-chlorophenothiazine (J. Het. Chem. 3, 345, 1966) for 2-acetylphenothiazine as starting material, the title product was obtained as a cream-colored solid, m.p.: 176°–177° C.

Analysis: Calc'd for $C_{16}H_{16}ClN_3O_2S$: C, 54.93; H, 4.61; Cl, 10.14; N, 12.01; S, 9.16. Found: C, 54.84; H, 4.58; Cl, 10.33; N, 12.18; S, 9.30.

EXAMPLE 18

N-[1-(10-acetyl-8-Chlorophenothiazin-2-yl)ethyl]-N-hydroxy urea

Following the procedures described in Example 14, Steps 1–2, but substituting 8-chloro-2,10-diacetylphenothiazine (J. Het. Chem. 3, 345, 1966) for 2-acetylphenoxathiin as starting material, the title product was obtained, m.p.: 157°–159° C.

What is claimed is:

1. A compound having the formula I:

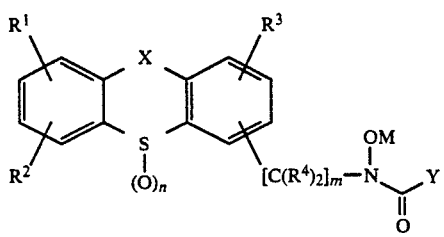

wherein:

$R^1$, $R^2$ and $R^3$ are independently:
 a) hydrogen,
 b) lower alkyl,
 c) lower cycloalkyl,
 d) lower alkoxy,
 e) lower alkanoyloxy,
 f) —$CF_3$
 g) —CN,
 h) —$NO_2$,
 i) —$OR^4$,
 j) —$N(R^4)_2$, —$NCOR^4$, —$N(R^4)CON(R^4)_2$,
 k) —$SR^5$, —$S(O)R^5$, —$S(O)_2R^5$, —$S(O)_2NR^4$,
 l) —$COR^4$, —$COOR^4$, —$CON(R^4)_2$,
 m) halogen;

$R^4$ is:
 a) hydrogen,
 b) $R^5$;

$R^5$ is:
 a) $C_1$-$C_4$ alkyl;

$R^6$ is:
 a) hydrogen,
 b) $C_1$ to $C_4$ alkyl,
 c) —$COR^4$,
 d) —$S(O)_2R^4$,
 e) —$C_1$-$C_4$ [alkyl] alkylene-Ar;

$R^7$ is:
 a) hydrogen,
 b) lower alkyl,
 c) Ar-lower alkyl;

Ar is:
 a) $R^1$ substituted phenyl,
 b) $R^1$ substituted furyl,
 c) $R^1$ substituted thienyl, X is:
 a) $X^1$,
 b) —CH=CH—,
 c) —$CH_2$—$CH_2$—,
 d) —$CH_2X^1$—,
 e) —$X^1CH_2$—,
 f) —$NR^7$;

$X^1$ is:
 a) O,
 b) S,
 c) S(O),
 d) $S(O)_2$,
 e) $NR^6$;

Y is:
 a) $R^4$,
 b) —$N(R^4)_2$;

M is:
 a) hydrogen,
 b) —COAr,
 c) —CO-alkyl;

m is 1 to 5;
n is 0 to 2;

or a pharmaceutically acceptable salt thereof.

2. A compound of claim 1 having the formula IX:

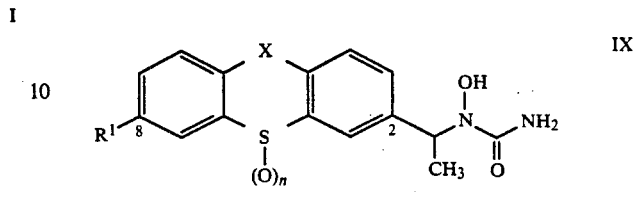

wherein the substituents are as follows:

| X | n | $R^1$ |
|---|---|---|
| O | 0 | H |
| O | 2 | H |
| O | 0 | Cl |
| O | 0 | Br |
| O | 0 | CN |
| $CH_2O$ | 0 | H |

3. A compound of claim 1 having the formula X:

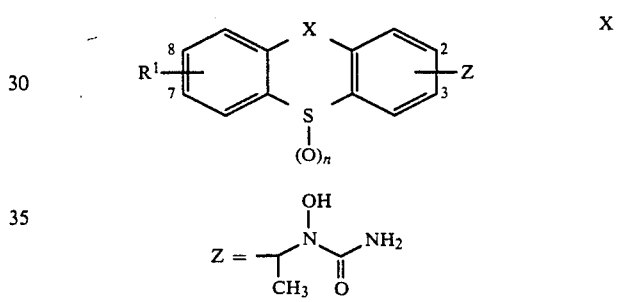

wherein the substituents are as follows:

| X | n | POSITION OF Z | $R^1$ |
|---|---|---|---|
| CH=CH | 0 | 3 | H |
| CH=CH | 2 | 3 | H |
| $CH_2$—$CH_2$ | 0 | 3 | H |
| $CH_2$—$CH_2$ | 0 | 2 | 7-$CO_2CH_3$H |
| $CH_2$—$CH_2$ | 0 | 2 | 7-$CO_2$H |
| $CH_2$—$CH_2$ | 2 | 2 | 7-$CON(CH_3)_2$ |
| NH | 0 | 2 | H |
| $NCH_3$ | 0 | 2 | H |
| $NCH_2C_6H_4$-4-$SCH_3$ | 0 | 2 | H |
| $NCH_2C_6H_4$-4-$S(O)_2CH_3$ | 0 | 2 | H |
| $NCH_3$ | 0 | 2 | 8-Cl |
| $NCOCH_3$ | 0 | 2 | 8-Cl |

4. A compound according to claim 1 which is any of the following compounds:
N-[1-(Phenoxathiin-2-yl)ethyl]-N-hydroxy urea,
N-[1-(10,10-Dioxophenoxathiin-2-yl)ethyl]-N-hydroxy urea,
N-[1-(8-Chlorophenoxathiin-2-yl)ethyl]-N-hydroxy urea,
N-[1-(8-Bromophenoxathiin-2-yl)ethyl]-N-hydroxy urea,
N-[1-(8-Cyanophenoxathiin-2-yl)ethyl]-N-hydroxy urea,
N-[1-(Dibenzo[b,f]thiepin-3-yl)ethyl]-N-hydroxy urea, N-[1-(5,5-Dioxodibenzo[b,f]thiepin-3-yl)ethyl]-N-hydroxy urea, N-[1-(10,11-Dihydrodibenzo[b,f]thiepin-3-yl)ethyl]-N-hydroxy urea, N-[1(6H-Dibenz[b,e][1,4]oxathiepin-2-yl]ethyl]-N-hydroxy urea, N-[1-(7-Carbomethoxy-10,11-dihydrodibenzo[b,f]thiepin-2-yl)ethyl]-N-hydroxy urea, N-[1-(7-Carboxy-10,11-dihydrodibenzo[b,f]thiepin-2-yl)ethyl]-N-hydroxy urea, N-[1-(7-Dimethylcarboxamido-5,5-dioxo-10,11-dihydrodibenzo[b,f]thiepin-2-yl)ethyl]-N-hydroxy urea, N-[1-(Phenothiazin-2-yl)ethyl]-N-hydroxy urea, N-[1-(10-Methylphenothiazin-2-yl)ethyl]-N-hydroxy urea, N-{1-[10-(4-Methylthiobenzyl)phenothiazin-2-yl]ethyl}-N-hydroxy urea, N-{-[10-(4-Methylsulfonylbenzyl)phenothiazin-2-yl]ethyl}-N-hydroxy urea, N-[1-(8-Chloro-10-methylphenothiazin-2-yl)ethyl]-N-hydroxy urea, or N-[1-(8-Chloro-10-acetylphenothiazin-2-yl)ethyl]-N-hydroxy urea.

5. A pharmaceutical composition for treatment of asthmatic, inflammatory or allergic conditions comprising a therapeutically effective amount of a compound of claim 1 and a pharmaceutically acceptable carrier.

6. A method of treating a mammal suffering from asthmatic, inflammatory, or allergic conditions comprising administration to said mammal of a therapeutically effective amount of a compound of claim 1.

7. The method of claim 6 wherein the mammal is a human.

8. A method for inhibiting 5-lipoxygenase or 12-lipoxygenase activity comprising administration to a mammal of a therapeutically effective amount of a compound of claim 1.

9. The method of claim 8 wherein the mammal is a human.

* * * * *

UNITED STATES PATENT AND TRADEMARK OFFICE
CERTIFICATE OF CORRECTION

PATENT NO. : 5,036,067

DATED : Jul. 30, 1991

INVENTOR(S) : Yves Girard; Pierre Hamel; Daniel Delorme

It is certified that error appears in the above-identified patent and that said Letters Patent is hereby corrected as shown below:

On the title page:

Please correct the Assignee to read: MERCK FROSST CANADA, INC. Kirkland, Quebec, CANADA Signed and Sealed this Second Day of March, 1993

*Attest:*

STEPHEN G. KUNIN

*Attesting Officer*     *Acting Commissioner of Patents and Trademarks*